(12) United States Patent
Iwasaki et al.

(10) Patent No.: US 12,032,229 B2
(45) Date of Patent: Jul. 9, 2024

(54) CONTACT LENS

(71) Applicant: SONY CORPORATION, Tokyo (JP)

(72) Inventors: Masanori Iwasaki, Kanagawa (JP);
Naoto Yamaguchi, Tokyo (JP);
Tsukasa Yoshimura, Tokyo (JP);
Masakazu Yajima, Kanagawa (JP);
Fumiko Shiga, Tokyo (JP); Ken
Hayakawa, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 190 days.

(21) Appl. No.: 16/753,689

(22) PCT Filed: Aug. 6, 2018

(86) PCT No.: PCT/JP2018/029412
§ 371 (c)(1),
(2) Date: Apr. 3, 2020

(87) PCT Pub. No.: WO2019/073676
PCT Pub. Date: Apr. 18, 2019

(65) Prior Publication Data
US 2020/0271956 A1 Aug. 27, 2020

(30) Foreign Application Priority Data
Oct. 13, 2017 (JP) .................. 2017-199360

(51) Int. Cl.
G02C 7/04 (2006.01)
A61B 5/00 (2006.01)
G02C 7/12 (2006.01)

(52) U.S. Cl.
CPC .............. *G02C 7/04* (2013.01); *A61B 5/6821* (2013.01); *G02C 7/12* (2013.01); *A61B 2562/0233* (2013.01)

(58) Field of Classification Search
CPC .. G02C 7/04; G02C 7/12; G02C 7/105; A61B 5/6821; A61B 2562/0233; A61B 3/063; A61B 3/112
See application file for complete search history.

(56) References Cited

U.S. PATENT DOCUMENTS 4,669,834 A * 6/1987 Richter .................. G02C 7/108
351/159.24
6,338,559 B1 1/2002 Williams et al.
(Continued)

FOREIGN PATENT DOCUMENTS

AU 5704201 A 11/2001
AU 2003256274 A 1/2004
(Continued)

OTHER PUBLICATIONS

WO 2014/178221 Machine Translation (Year: 2014).*
(Continued)

*Primary Examiner* — Darryl J Collins
*Assistant Examiner* — Matthew Y Lee
(74) *Attorney, Agent, or Firm* — CHIP LAW GROUP

(57) ABSTRACT

A contact lens according to an embodiment of the present disclosure includes: a lens unit to be placed on an eyeball; and an optical device that is mainly provided in a circular region opposed to a pupil that becomes small by contraction in a case where the lens unit is placed on the eyeball, and provides an action that is different from an action of the lens unit to light entering the eyeball.

4 Claims, 10 Drawing Sheets

(56) References Cited

U.S. PATENT DOCUMENTS

| | | | |
|---|---|---|---|
| 2003/0142267 | A1 | 7/2003 | Gemert et al. |
| 2004/0001181 | A1 | 1/2004 | Kunzler et al. |
| 2012/0194780 | A1* | 8/2012 | Back .................. G02C 7/042 351/159.73 |
| 2013/0265507 | A1* | 10/2013 | Ford .................. G02C 7/044 349/13 |
| 2014/0022505 | A1 | 1/2014 | Pugh et al. |
| 2014/0243971 | A1* | 8/2014 | Pugh .................. G02C 7/04 623/6.22 |
| 2014/0268014 | A1* | 9/2014 | Pugh .................. G02B 27/0172 351/158 |
| 2015/0148650 | A1 | 5/2015 | Pugh |
| 2015/0186701 | A1* | 7/2015 | Otis .................. G06K 19/0717 340/10.1 |
| 2015/0192800 | A1 | 7/2015 | Dirk et al. |
| 2015/0286073 | A1 | 10/2015 | Blum |
| 2016/0299357 | A1 | 10/2016 | Hayashi et al. |
| 2017/0280067 | A1* | 9/2017 | Mingus, III .......... G02C 7/04 |
| 2017/0285370 | A1* | 10/2017 | Leip .................. G02C 7/102 |
| 2018/0088351 | A1* | 3/2018 | Kennedy ............. G02C 7/083 |
| 2018/0095296 | A1* | 4/2018 | Lin .................. A61F 9/0017 |

FOREIGN PATENT DOCUMENTS

| | | |
|---|---|---|
| AU | 2003297878 A1 | 6/2004 |
| AU | 2010308489 A1 | 12/2011 |
| AU | 2013206817 A1 | 2/2014 |
| AU | 2014265094 A1 | 6/2015 |
| BR | 102014029034 A2 | 9/2015 |
| CA | 2407082 A | 11/2001 |
| CA | 2490919 A | 1/2004 |
| CA | 2761855 A1 | 4/2011 |
| CA | 2821191 A1 | 1/2014 |
| CA | 2871204 A1 | 5/2015 |
| CN | 1426286 A | 6/2003 |
| CN | 1732078 A | 2/2006 |
| CN | 102472899 A | 5/2012 |
| CN | 103576336 A | 2/2014 |
| CN | 104644149 A | 5/2015 |
| CN | 105122094 A | 12/2015 |
| CN | 106415372 A | 2/2017 |
| EP | 1278451 A1 | 1/2003 |
| EP | 1518141 A1 | 3/2005 |
| EP | 1575761 A2 | 9/2005 |
| EP | 2425294 A1 | 3/2012 |
| EP | 2687898 A1 | 1/2014 |
| EP | 2876489 A1 | 5/2015 |
| EP | 2914990 A2 | 9/2015 |
| EP | 3090304 A1 | 11/2016 |
| JP | 2003-532150 A | 10/2003 |
| JP | 2005-531810 A | 10/2005 |
| JP | 2006-503338 A | 1/2006 |
| JP | 2013-501963 A | 1/2013 |
| JP | 2014-021500 A | 2/2014 |
| JP | 2015-107323 A | 6/2015 |
| JP | 2015-537240 A | 12/2015 |
| JP | 2016-053724 A | 4/2016 |
| JP | 2017-505648 A | 2/2017 |
| JP | 2017102435 A | 6/2017 |
| JP | 2017114094 | 6/2017 |
| JP | 2017219847 A | 12/2017 |
| KR | 10-2005-0085481 A | 8/2005 |
| KR | 10-2012-0035159 A | 4/2012 |
| KR | 10-2014-0011285 A | 1/2014 |
| KR | 10-2015-0059616 A | 6/2015 |
| KR | 10-2015-0079907 A | 7/2015 |
| MX | PA02010624 A | 10/2003 |
| MX | 2011011795 A | 2/2012 |
| RU | 2013131643 A | 1/2015 |
| RU | 2014146988 A | 6/2016 |
| RU | 2016131279 A | 2/2018 |
| SG | 175913 A1 | 12/2011 |
| TW | 500604 B | 9/2002 |
| TW | 201411223 A | 3/2014 |
| TW | 201534266 A | 9/2015 |
| WO | 2001/082791 A1 | 11/2001 |
| WO | 2004/003636 A1 | 1/2004 |
| WO | 2004/052631 A2 | 6/2004 |
| WO | 2011/049642 A1 | 4/2011 |
| WO | 2014/011581 A2 | 1/2014 |
| WO | 2014/071179 A2 | 5/2014 |
| WO | 2014/178221 A1 | 11/2014 |
| WO | WO 2014/178221 * 11/2014 .............. G02C 7/04 |
| WO | 2015/102740 A1 | 7/2015 |

OTHER PUBLICATIONS

International Search Report and Written Opinion of PCT Application No. PCT/JP2018/029412, dated Nov. 6, 2018, 19 pages of ISRWO.

* cited by examiner

[ FIG. 1 ]
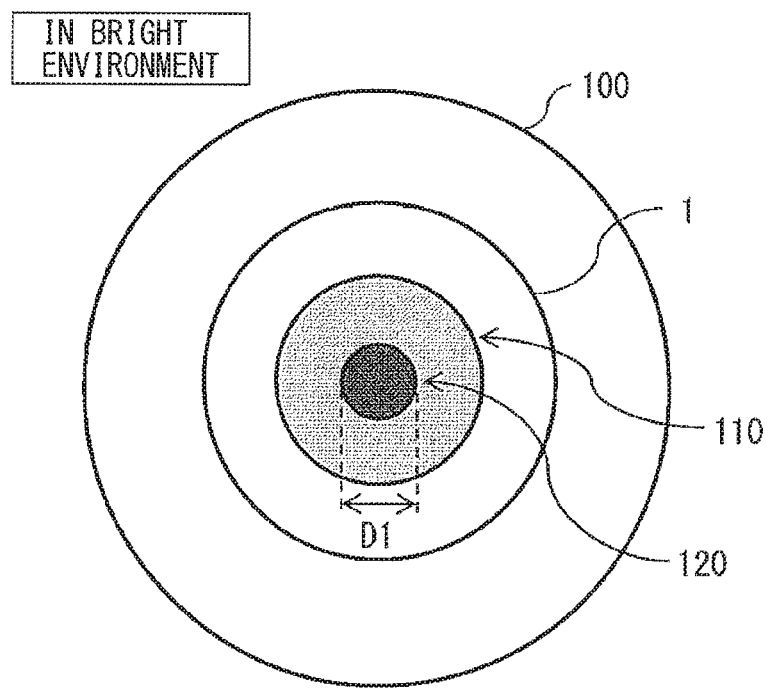
[ FIG. 2 ]
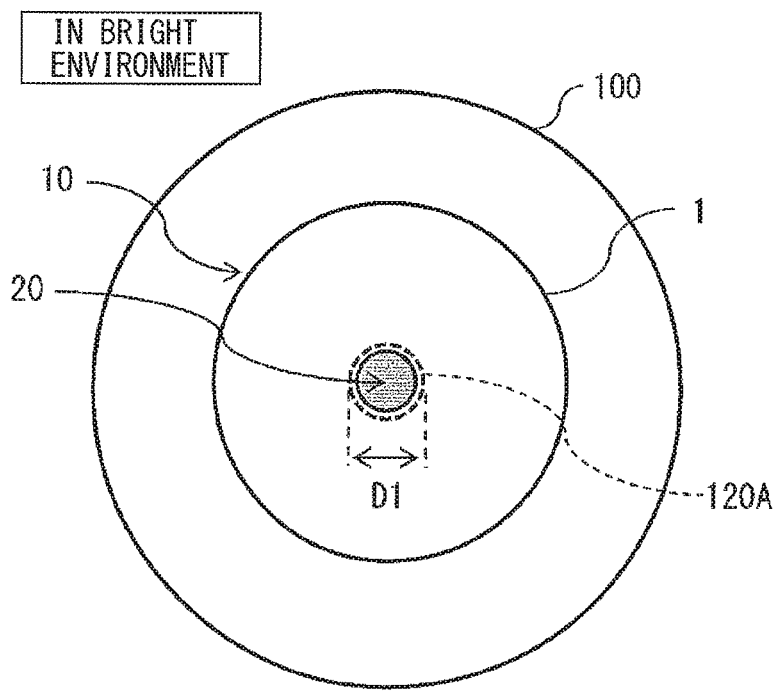

[ FIG. 3 ]
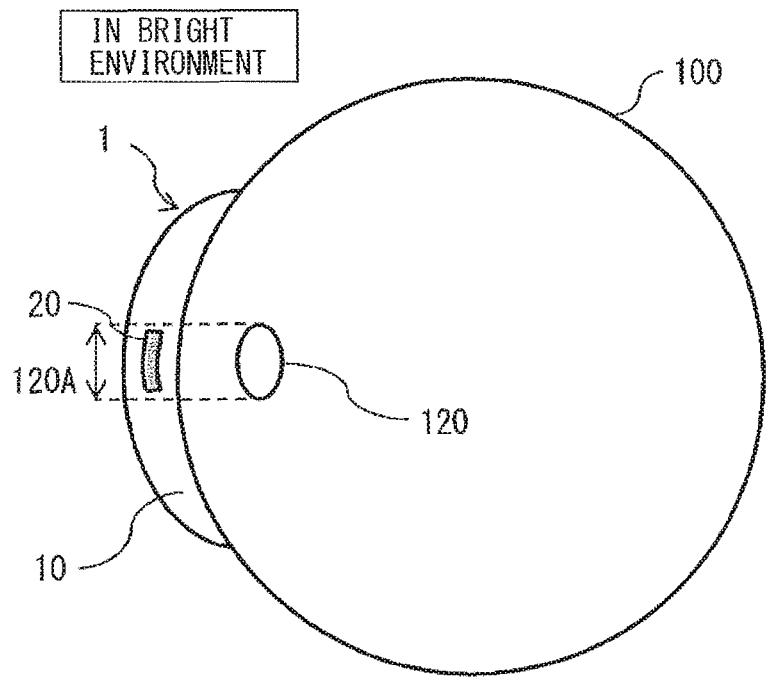
[ FIG. 4 ]
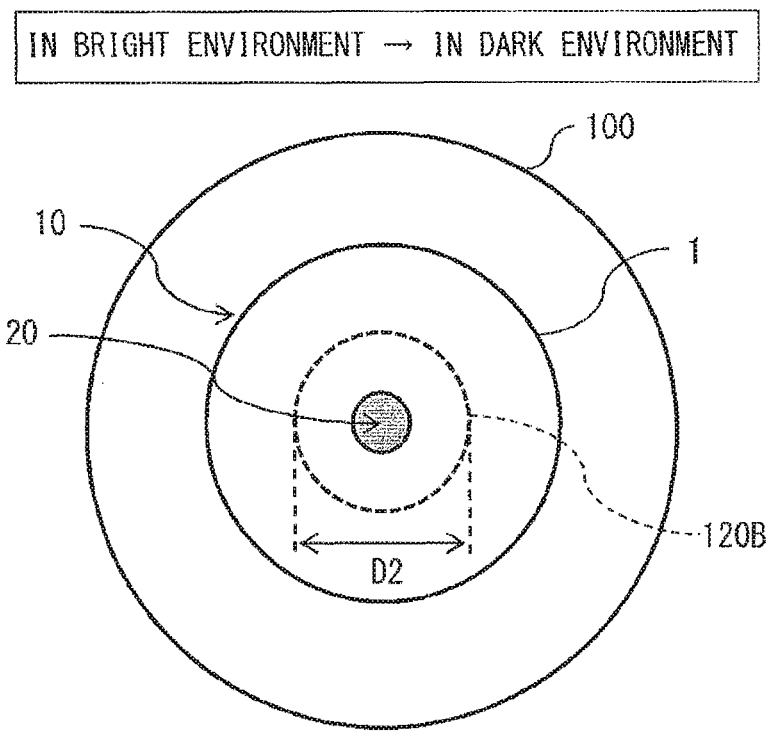

[ FIG. 5 ]
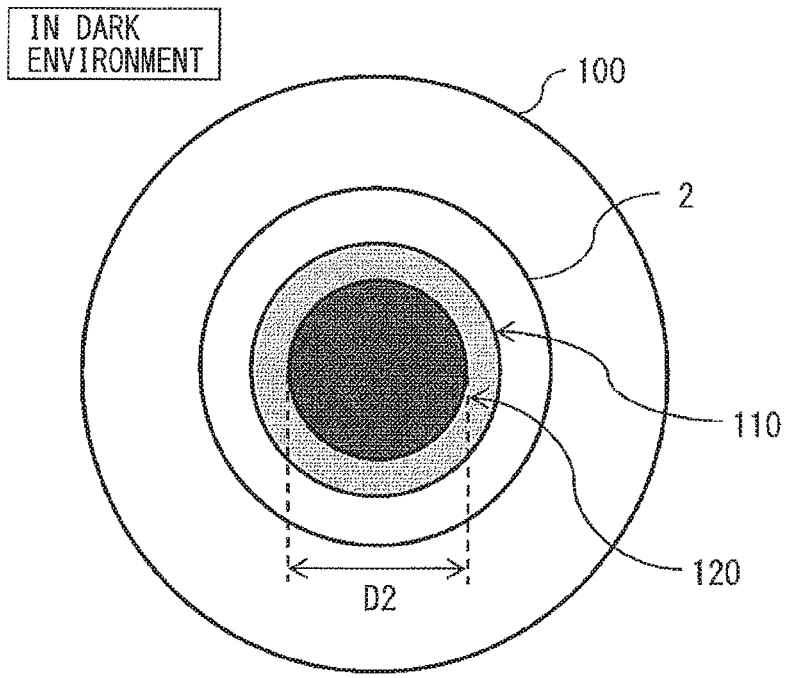
[ FIG. 6 ]
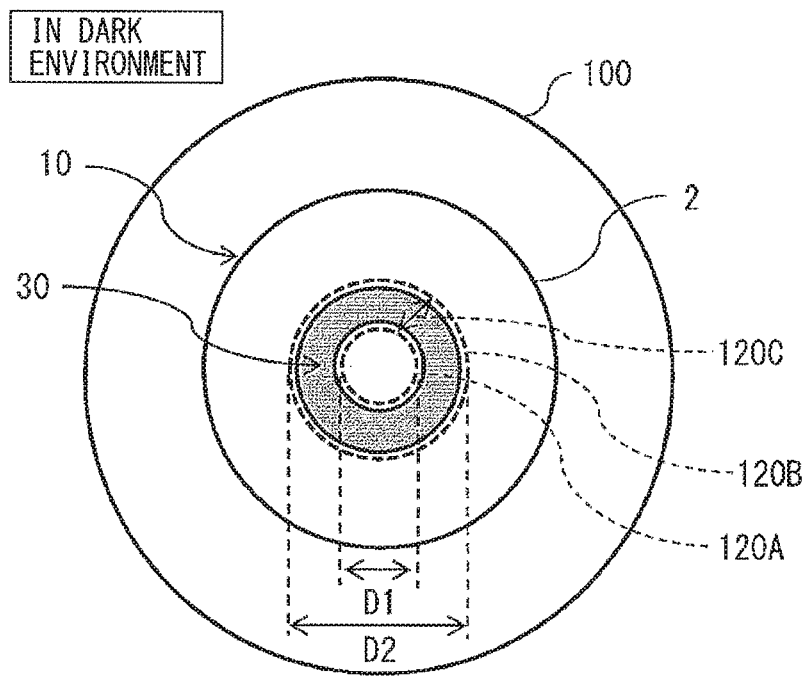

[FIG. 7]
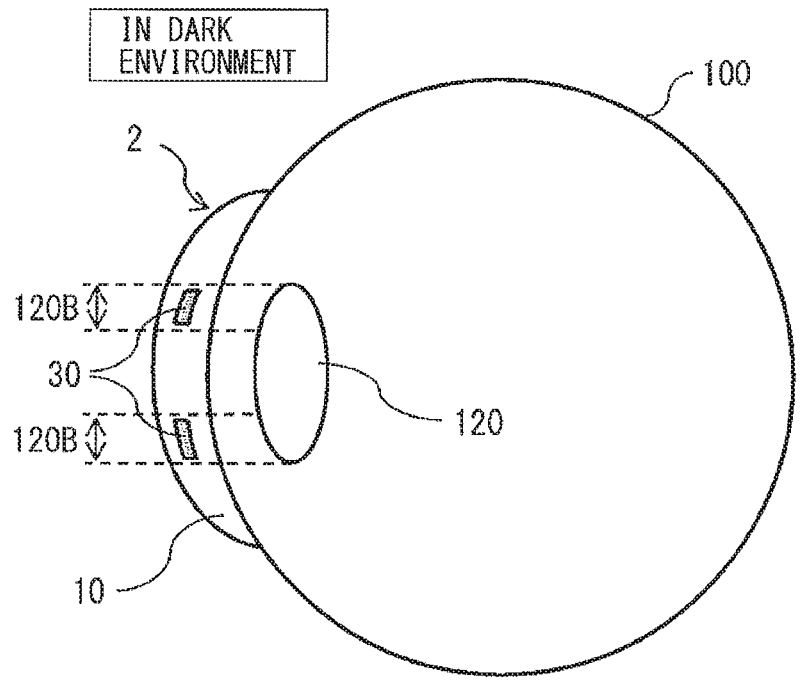
[FIG. 8]
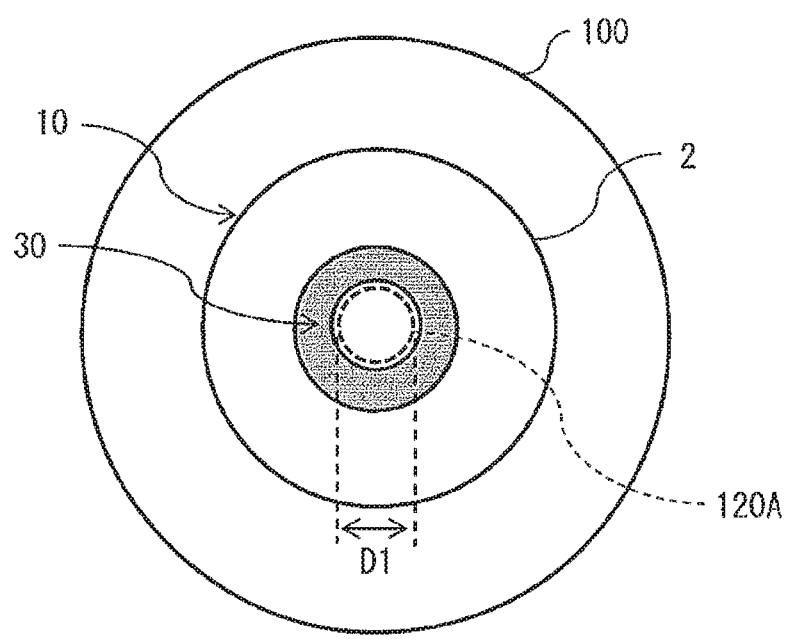

[ FIG. 9 ]
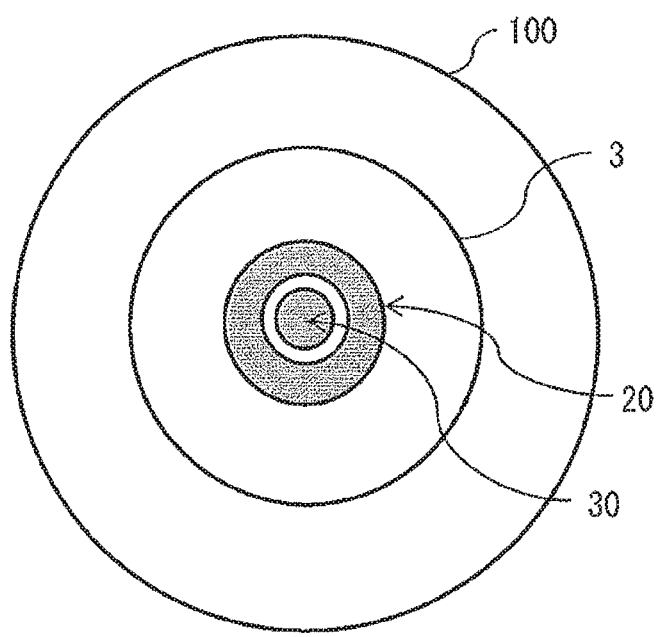
[ FIG. 10 ]
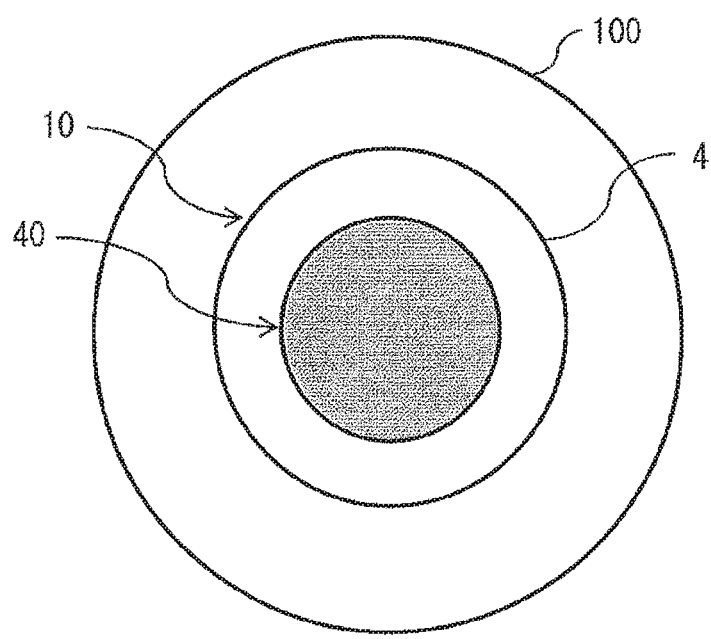

[ FIG. 11 ]
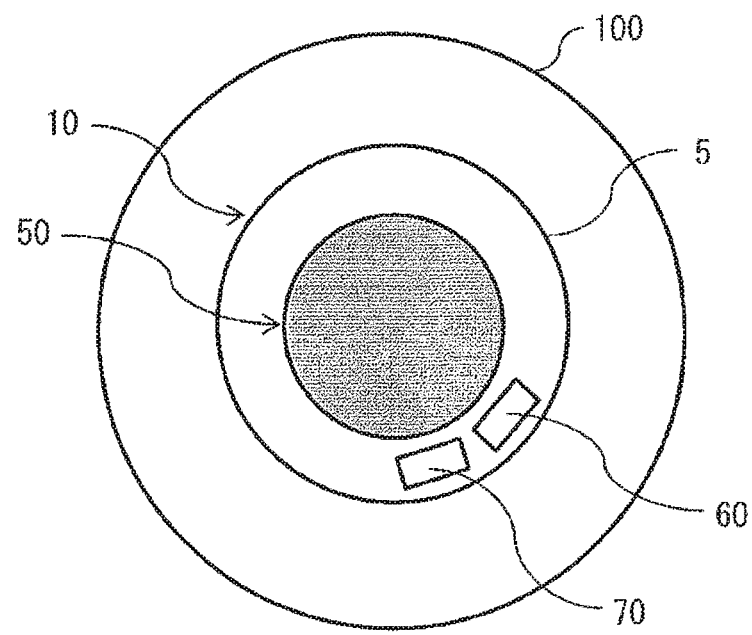
[ FIG. 12 ]
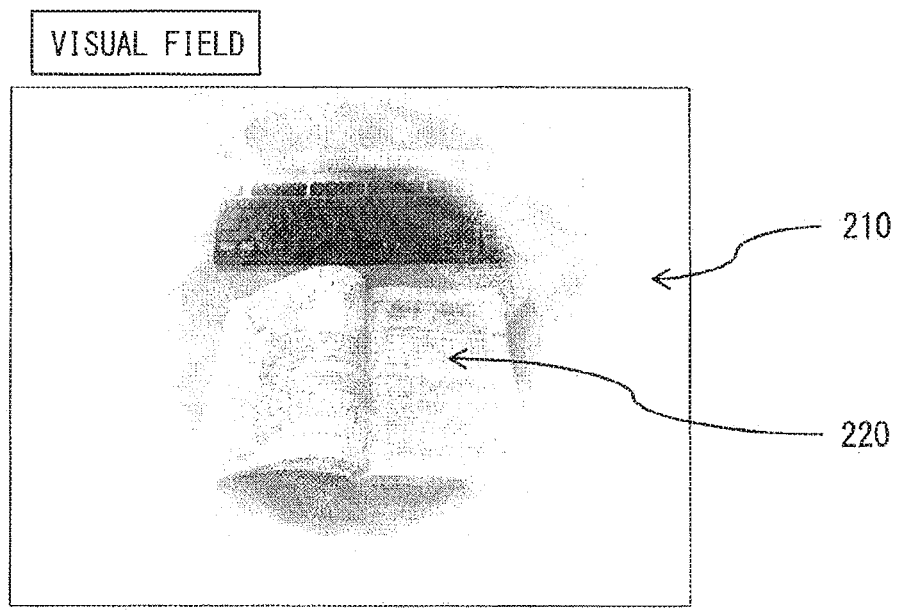

[ FIG. 13 ]
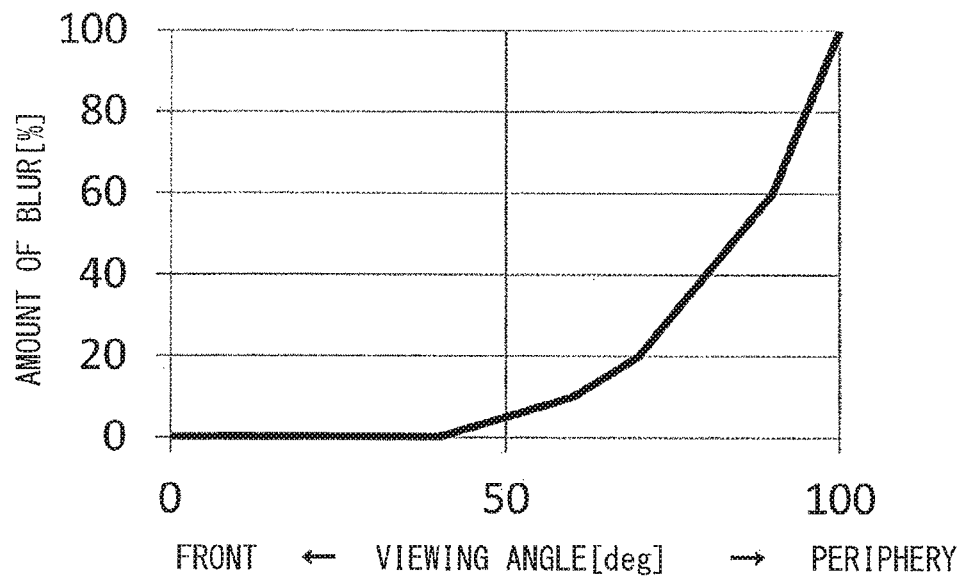
[ FIG. 14 ]
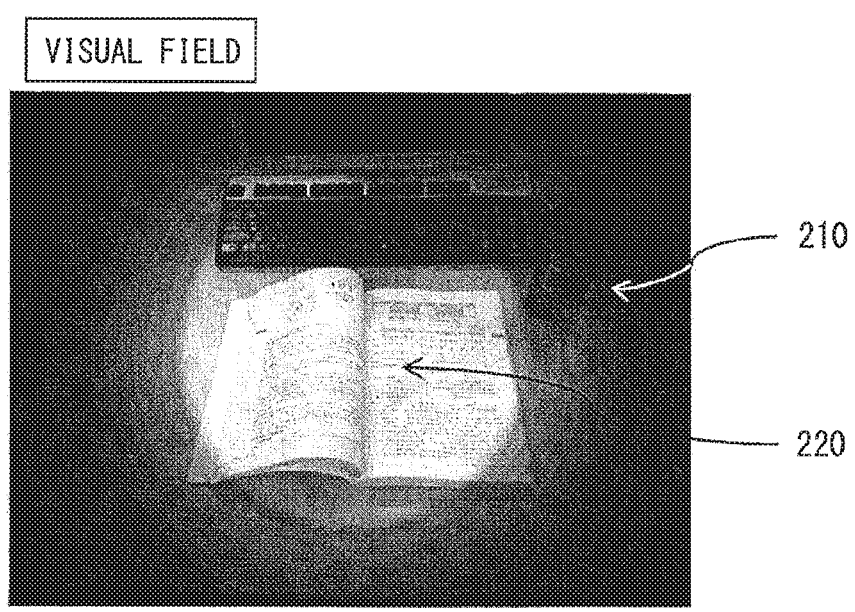

[ FIG. 15 ]
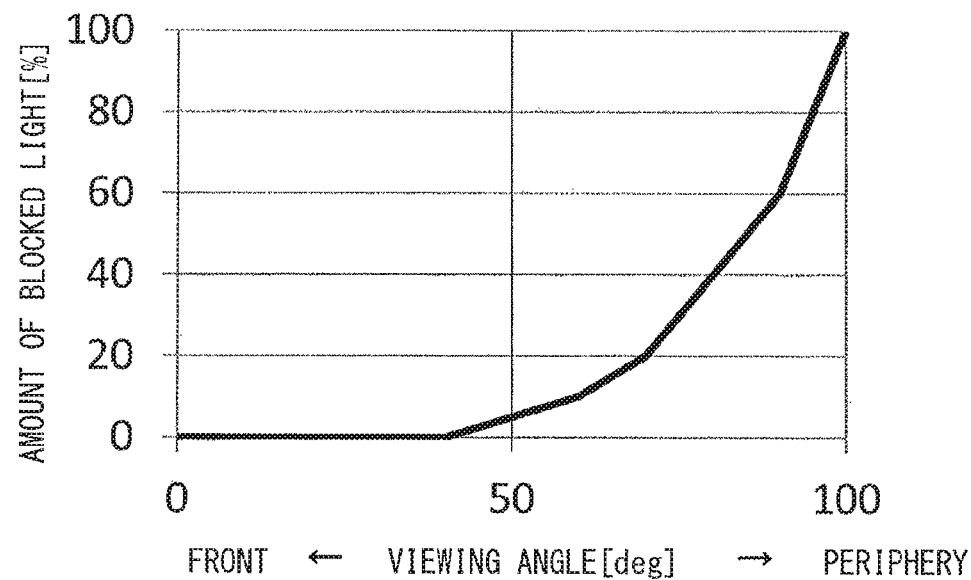
[ FIG. 16 ]
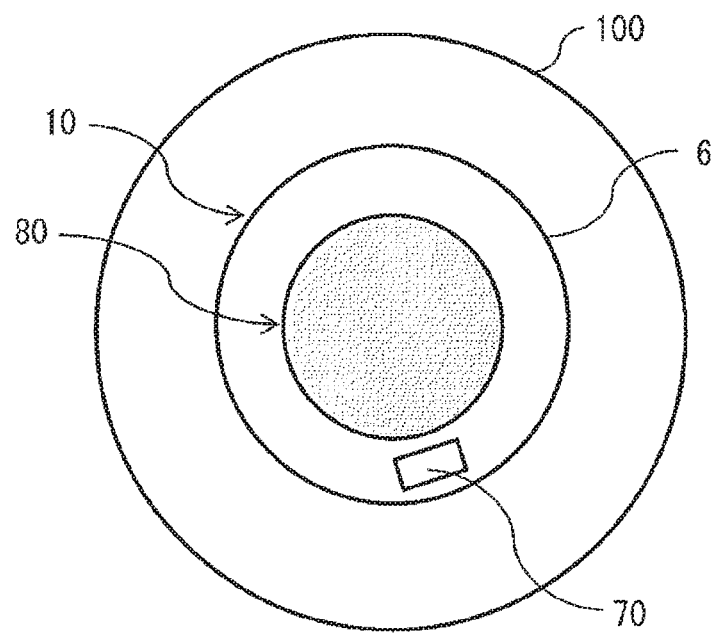

[ FIG. 17 ]
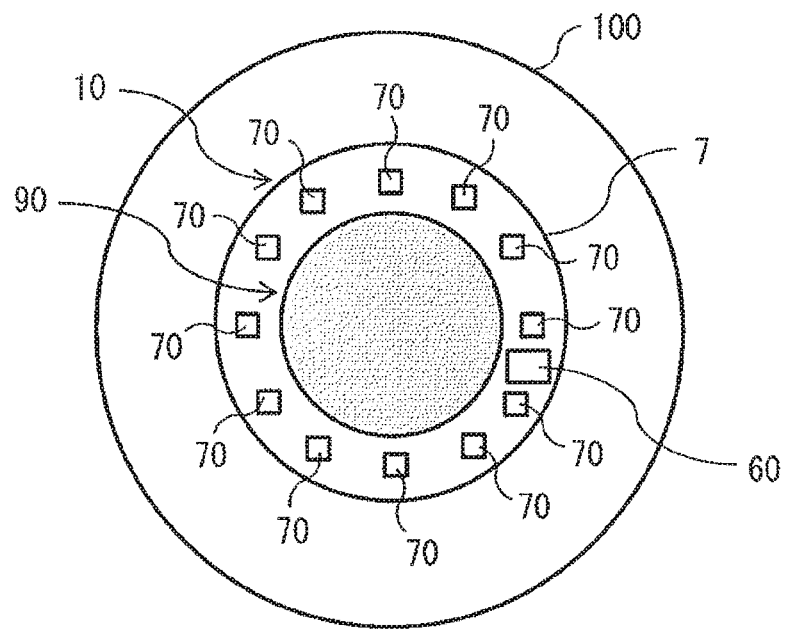
[ FIG. 18 ]
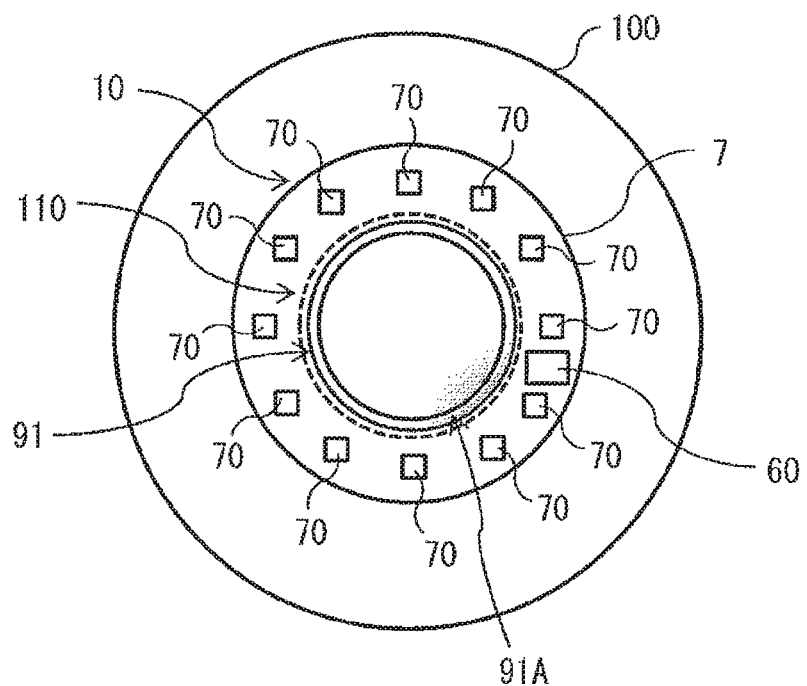

[ FIG. 19 ]
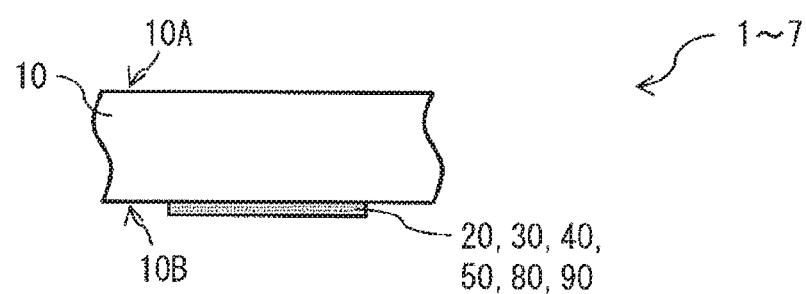
[ FIG. 20 ]
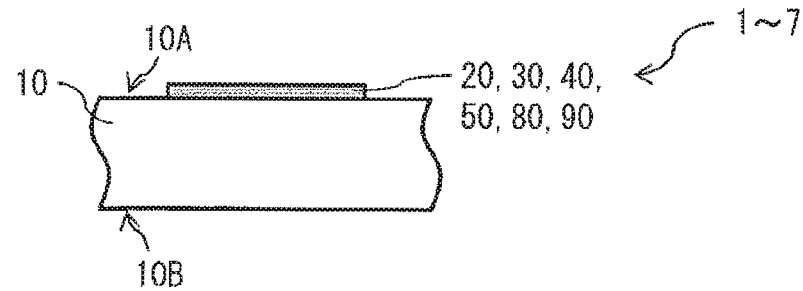

CONTACT LENS

CROSS REFERENCE TO RELATED APPLICATIONS

This application is a U.S. National Phase of International Patent Application No. PCT/JP2018/029412 filed on Aug. 6, 2018, which claims priority benefit of Japanese Patent Application No. JP 2017-199360 filed in the Japan Patent Office on Oct. 13, 2017. Each of the above-referenced applications is hereby incorporated herein by reference in its entirety.

TECHNICAL FIELD

The present disclosure relates to a contact lens.

BACKGROUND ART

Until now, through the use of glasses, for example, a specific polarization component included in light entering an eyeball has been cut off or an amount of the light entering the eyeball has been adjusted.

CITATION LIST

Patent Literature

PTL 1: Japanese Unexamined Patent Application Publication No. 2016-053724

SUMMARY OF THE INVENTION

However, due to a violent motion, glasses may be removed from a head and drop. Therefore, it is desirable to provide a contact lens that is able to respond to the violent motion or the like, while providing a predetermined action to light entering an eyeball.

A first contact lens according to an embodiment of the present disclosure includes: a lens unit to be placed on an eyeball; and an optical device that is mainly provided in a circular region opposed to a pupil that becomes small by contraction in a case where the lens unit is placed on the eyeball, and provides an action that is different from an action of the lens unit to light entering the eyeball.

In the first contact lens according to the embodiment of the present disclosure, the optical device is mainly provided in the circular region opposed to the pupil that becomes small by contraction in the case where the lens unit is placed on the eyeball. The optical device provides the action that is different from the action of the lens unit to the light entering the eyeball. Accordingly, a user feels an effect of the optical device only in a case where the pupil becomes small in a bright environment.

A second contact lens according to an embodiment of the present embodiment includes: a lens unit to be placed on an eyeball; and an optical device that is mainly provided in a ring region opposed to an outer edge of a pupil that becomes large by expansion in a case where the lens unit is placed on the eyeball, and provides an action that is different from an action of the lens unit to light entering the eyeball.

In the second contact lens according to the embodiment of the present disclosure, the optical device is mainly provided in the ring region opposed to the outer edge of the pupil that becomes large by expansion in the case where the lens unit is placed on the eyeball. The optical device provides the action that is different from the action of the lens unit to the light entering the eyeball. Accordingly, the user feels an effect of the optical device only in a case where the pupil becomes large in a dark environment.

A third contact lens according to an embodiment of the present disclosure includes: a lens unit to be placed on an eyeball; and an optical device that is provided in the lens unit, and has viewing angle characteristics that make an amount of blur in a peripheral portion of a visual field larger than an amount of blur in a central portion of the visual field.

In the third contact lens according to the embodiment of the present disclosure, in the case where the lens unit is placed on the eyeball, the amount of blur in the peripheral portion of the visual field is larger than the amount of blur in the central portion of the visual field. Accordingly, while the user is less likely to be distracted by an event in the peripheral portion of the visual field, the user easily concentrates on an event in the central portion of the visual field.

A fourth contact lens according to an embodiment of the present disclosure includes: a lens unit to be placed on an eyeball; a sensor device that senses a change in an external environment; and an optical device that is provided in the lens unit, and changes a degree of an own action of the optical device on the basis of a sensing signal outputted from the sensor device.

In the fourth contact lens according to the embodiment of the present disclosure, in a case where the lens unit is placed on the eyeball, the degree of the action of the optical device changes on the basis of the sensing signal outputted from the sensor device. Accordingly, the user feels an effect of the optical device upon a change in the external environment.

A fifth contact lens according to an embodiment of the present disclosure includes: a lens unit to be placed on an eyeball; and an optical device that is provided in the lens unit, and performs wavelength conversion, wavelength selection, or expansion of wavelength distribution on light entering the eyeball.

In the fifth contact lens according to the embodiment of the present embodiment, in the case where the lens unit is placed on the eyeball, the wavelength conversion, the wavelength selection, or the expansion of the wavelength distribution is performed on the light entering the eyeball. Accordingly, the user obtains a predetermined optical effect with a small amount of visible light attenuation, such as the wavelength conversion, the wavelength selection, or the expansion of the wavelength distribution.

A sixth contact lens according to an embodiment of the present disclosure includes: a lens unit to be placed on an eyeball; a light-emitting device provided in the lens unit; a sensor device that senses a change in an external environment; and a control unit that controls light emission of the light-emitting device on the basis of a sensing signal outputted from the sensor device.

In the sixth contact lens according to the embodiment of the present disclosure, the light emission of the light-emitting device is controlled on the basis of the sensing signal outputted from the sensor device. This allows the user to know a change in an external environment from, for example, a light-emitting position in the light-emitting device.

The first contact lens to the sixth contact lens according to the respective embodiments of the present disclosure make it possible to respond to a violent motion or the like, while providing a predetermined action to the light entering the eyeball. It is to be noted that the effects described here are not necessarily limited, and any effect described herein may be provided.

BRIEF DESCRIPTION OF DRAWINGS

FIG. 1 is a front view of an example of a condition in which a contact lens according to a first embodiment of the present disclosure is placed on an eyeball in a bright environment.

FIG. 2 is a front view of an example of the condition in which the contact lens of FIG. 1 is placed on the eyeball in the bright environment.

FIG. 3 is a cross-sectional diagram illustrating an example of a cross-sectional configuration of the contact lens of FIG. 2 and the eyeball.

FIG. 4 is a front view of an example of a condition in which the contact lens of FIG. 1 is placed on the eyeball in a case where transition is made from the bright environment to a dark environment.

FIG. 5 is a front view of an example of a condition in which a contact lens according to a second embodiment of the present disclosure is placed on the eyeball in the dark environment.

FIG. 6 is a front view of an example of the condition in which the contact lens of FIG. 5 is placed on the eyeball in the dark environment.

FIG. 7 is a cross-sectional diagram illustrating an example of a cross-sectional configuration of the contact lens of FIG. 5 and the eyeball.

FIG. 8 is a front view of an example of a condition in which the contact lens of FIG. 5 is placed on the eyeball in a case where transition is made from the dark environment to the bright environment.

FIG. 9 is a front view of an example of a condition in which a contact lens according to a third embodiment of the present disclosure is placed on the eyeball.

FIG. 10 is a front view of an example of a condition in which a contact lens according to a fourth embodiment of the present disclosure is placed on the eyeball.

FIG. 11 is a front view of an example of a condition in which a contact lens according to a fifth embodiment of the present disclosure is placed on the eyeball.

FIG. 12 is a diagram illustrating an example of a visual field in a case where the contact lens of FIG. 10 is placed on the eyeball.

FIG. 13 is a diagram illustrating an example of an amount of blur of the visual field of FIG. 12.

FIG. 14 is a diagram illustrating an example of the visual field in a case where the contact lens of FIG. 10 is placed on the eyeball.

FIG. 15 is a diagram illustrating an example of an amount of blocked light of the visual field of FIG. 14.

FIG. 16 is a front view of an example of a condition in which a contact lens according to a sixth embodiment of the present disclosure is placed on the eyeball.

FIG. 17 is a front view of an example of an example of a condition in which a contact lens according to a seventh embodiment of the present disclosure is placed on the eyeball.

FIG. 18 is a front view of a modification example of the contact lens of FIG. 17.

FIG. 19 is a cross-sectional diagram illustrating a modification example of a cross-sectional configuration of the contact lens of FIG. 2, FIG. 6, FIG. 9, FIG. 10, FIG. 11, FIG. 16, or FIG. 17.

FIG. 20 is a cross-sectional diagram illustrating a modification example of the cross-sectional configuration of the contact lens of FIG. 2, FIG. 6, FIG. 9, FIG. 10, FIG. 11, FIG. 16, or FIG. 17.

MODES FOR CARRYING OUT THE INVENTION

In the following, some embodiments of the present disclosure are described in detail with reference to the drawings. It is to be noted that description is given in the following order.
1. First Embodiment
An example in which an optical device is provided in a middle of a lens unit (FIG. 1 to FIG. 4)
2. Second Embodiment
An example in which an optical device is provided on an outer edge of the lens unit (FIG. 5 to FIG. 8)
3. Third Embodiment
An example in which an optical device is provided in each of the middle and the outer edge of the lens unit (FIG. 9)
4. Fourth Embodiment
An example in which an optical device is provided in a wide range of the lens unit (FIG. 10)
5. Fifth Embodiment
An example in which a control unit that controls an optical device and a sensor device are provided (FIG. 11 to FIG. 15)
6. Sixth Embodiment
An example in which an optical device is controlled through sensor output
7. Seventh Embodiment (FIG. 16)
An example in which a plurality of sensor devices is equipped (FIG. 17 and FIG. 18)
8. Modification Examples
An example in which an optical device is provided on a front face and a rear face of the lens unit (FIG. 19 and FIG. 20)

1. First Embodiment

[Configuration]

Description is given of a contact lens 1 according to a first embodiment of the present disclosure. FIG. 1, FIG. 2, and FIG. 4 illustrate an example of a condition in which the contact lens 1 is placed on an eyeball 100. FIG. 3 illustrates an example of a cross-sectional configuration of the contact lens 1 and the eyeball 100. The eyeball 100 has an iris 110 and a pupil 120, for example. FIG. 1 and FIG. 2 illustrate, by an example, a condition in which the pupil 120 contracts in a bright environment and a diameter of the pupil 120 (or a circular region opposed to the pupil 120) is D1. FIG. 2 illustrates, by an example, components of the contact lens 1. FIG. 4 illustrates, by an example, a condition in which the pupil 120 expands in a case where transition is made from the bright environment to a dark environment, and the diameter of the pupil 120 (or the circular region opposed to the pupil 120) is D2.

The contact lens 1 includes a lens unit 10 to be placed on the eyeball 100 and an optical device 20 provided in the lens unit 10. The lens unit 10 has a curved shape that follows a surface shape of the eyeball. The lens unit 10 is circular-shaped as viewed from front, for example. A diameter of the lens unit 10 has a value larger than a diameter D1 of the outer edge of the pupil 120. The lens unit 10 may be a lens having a vision correction function for correcting myopia, hyperopia, astigma, or the like, or an optically transparent base material not having such a vision correction function. The lens unit 10 includes an optically transparent resin, for example, and has a role as a supporting base material that supports the optical device 20.

The optical device 20 is formed at, for example, a middle of the lens unit 10. The optical device 20 is mainly provided in a circular region 120A opposed to the pupil 120 that becomes small by contraction in the bright environment in a case where the lens unit 10 is placed on the eyeball 100, for example. That is, the optical device 20 is disposed at a position where the optical device 20 roughly covers a region opposed to the pupil 120, for example, in a case where the pupil 120 contracts in the bright environment and the diameter of the pupil 120 becomes D1. The optical device 20 is provided within the lens unit 10, for example. For example, the optical device 20 is circular-shaped as viewed from the front. It is to be noted that the optical device 20 may be in any shape other than a circular shape, and may be elliptically-shaped or polygonal-shaped, for example.

The optical device 20 is a device that provides an action that is different from an action of the lens unit 10 to the light entering the eyeball 100. The optical device 20 performs polarization separation, light volume attenuation, wavelength conversion, wavelength selection, or expansion of wavelength distribution, or the like, for example.

In a case where the optical device 20 has a polarization separation function, the optical device 20 includes, for example, a polarizing lens that selectively attenuates light reflected at a ground surface or a water surface, from light that has entered the optical device 20.

In a case where the optical device 20 has a light volume attenuation function, the optical device 20 includes, for example, an ND (Neutral Density) filter that absorbs the light that has entered the optical device 20.

In a case where the optical device 20 has a wavelength conversion function, the optical device 20 includes, for example, a wavelength conversion film that converts ultraviolet rays included in the light that has entered the optical device 20 to visible light (blue light, for example) or a wavelength conversion film that converts infrared rays included in the light that has entered the optical device 20 to visible light (red light, for example). In the case where the optical device 20 has the wavelength conversion function, the optical device 20 includes, for example, a wavelength conversion film that converts the light included in the light that has entered the optical device 20 to a predetermined wavelength band (for example, a wavelength band visible by those who are partially color-blind) in a visible region.

In a case where the optical device 20 has a wavelength selection function, the optical device 20 may include, for example, a wavelength selection filter that selectively transmits light in a predetermined wavelength band included in the light that has entered the optical device 20. Examples of the wavelength selection filter include a filter that attenuates ultraviolet light, a filter that attenuates infrared light, a filter that attenuates light in a predetermined wavelength band of visible light, or the like.

In a case where the optical device 20 has a wavelength distribution expansion function, the optical device 20 includes, for example, an optical component that makes it possible to expand a band of wavelength distribution included in the light that has entered the optical device 20 and distinguish a subtle color difference in the light that has entered the optical device 20.

[Effects]

In the following, description is given of effects of the contact lens 1 of the present embodiment.

Until now, through the use of glasses, for example, a specific polarization component included in light entering the eyeball has been cut off or an amount of the light entering the eyeball has been adjusted. However, due to a violent motion, the glasses may be removed from a head and drop.

In contrast, in the present embodiment, functions applied to the glasses are provided in the contact lens 1. This makes it possible to respond to the violent motion or the like, while providing a predetermined action to the light entering the eyeball 100.

Furthermore, in the present embodiment, the optical device 20 is mainly provided in the circular region 120A opposed to the pupil 120 that becomes small by contraction in a case where the lens unit 10 is placed on the eyeball 100. The optical device 20 provides the action that is different from the action of the lens unit 10 to the light entering the eyeball 100. Accordingly, a user feels the effects of the optical device 20 only in a case where the pupil 120 becomes small in the bright environment. As a result, for example, it is possible to cause the user to feel, in the bright environment, an optical effect that is necessary in the bright environment and to prevent the user from feeling the optical effect that is rather not necessary in other environments (for example, a dark environment). Thus, in the present embodiment, it is possible to cause the user to feel, when necessary, the optical effect that is exerted in the glasses independent of the environment.

In addition, in the present embodiment, the optical device 20 provided in the lens unit 10 exhibits the function of, for example, the polarization separation, the light volume attenuation, the wavelength conversion, the wavelength selection, or the expansion of the wavelength distribution. This makes it possible to cause the user to feel, when necessary (in the bright environment), the optical effect that is exerted in the glasses independent of the environment.

Moreover, in the present embodiment, the optical device 20 is provided within the lens unit 10. Accordingly, the presence of the optical device 20 makes it possible to prevent projections and depressions from being generated on the surface of the lens unit 10. Hence, it is possible to avoid worsening of user's feeling of use of the contact lens 1 due to the presence of the optical device 20.

2. Second Embodiment

In the following, description is given of a contact lens 2 according to a second embodiment of the present disclosure. FIG. 5, FIG. 6, and FIG. 8 illustrate an example of a condition in which the contact lens 2 is placed on the eyeball 100. FIG. 7 illustrates an example of a cross-sectional configuration of the contact lens 2 and the eyeball 100. FIG. 5 and FIG. 6 illustrate, by an example, a condition in which the pupil 120 contracts in the dark environment and the diameter of the pupil 120 is D2 (D2<D1). FIG. 7 illustrates, by an example, components of the contact lens 2. FIG. 8 illustrates, by an example, a condition in which the pupil 120 contracts in a case where transition is made from the bright environment to the dark environment, and the diameter of the pupil 120 (or the circular region opposed to the pupil 120) is D1.

The contact lens 2 includes the lens unit 10 to be placed on the eyeball 100 and an optical device 30 provided in the lens unit 10. The diameter of the lens unit 10 has a value larger than a diameter D2 of the outer edge of the pupil 120. The lens unit 10 includes, for example, an optically transparent resin and has a role as a supporting base material that supports the optical device 30.

The optical device 30 is formed avoiding a middle of the lens unit 10, for example. The optical device 30 is mainly provided in a ring region 120C opposed to an outer edge region of the pupil 120 that becomes large by expansion in the dark environment in a case where the lens unit 10 is placed on the eyeball 100, for example. The ring region 120C is a band-shaped region between the outer edge of the circular region 120B in a case where the diameter of the pupil 120 is D2 and the outer edge of the circular region 120A in a case where the diameter of the pupil 120 is D1. That is, the optical device 30 is, for example, disposed at a position where the optical device 30 roughly covers the outer edge region of the pupil 120, for example, in a case where the pupil 120 contracts in the dark environment and the diameter of the pupil 120 becomes D2. In addition, for example, in a case where the pupil 120 expands in the bright environment and the diameter of the pupil 120 is D1, the optical device 30 is disposed avoiding the pupil 120. The optical device 30 is provided within the lens unit 10, for example. The optical device 30 is annular-shaped as viewed from the front. It is to be noted that the optical device 30 may be in any shape other than an annular shape and may be elliptical ring shaped or polygonal ring shaped, for example.

The optical device 30 is a device that provides an action that is different from an action of the lens unit 10 to the light entering the eyeball 100. The optical device 30 performs light volume amplification, contrast emphasis, wavelength conversion, wavelength selection, or expansion of wavelength distribution, for example.

In a case where the optical device 30 has a light volume amplification function, the optical device 30 includes, for example, a device that amplifies a visible light component included in light that has entered the optical device 30.

In a case where the optical device 30 includes a contrast emphasis function, the optical device 30 includes, for example, a device that emphasizes a difference in contrast between a high-luminance portion and a low-luminance portion of the light that has entered the optical device 30.

In a case where the optical device 30 has a wavelength conversion function, the optical device 30 includes, for example, a wavelength conversion film that converts ultraviolet rays included in the light that has entered the optical device 30 to visible light (blue light, for example) or a wavelength conversion film that converts infrared rays included in the light that has entered the optical device 30 to visible light (red light, for example). In the case where the optical device 30 has the wavelength conversion function, the optical device 30 includes, for example, a wavelength conversion film that converts light included in the light that has entered the optical device 30 to a predetermined wavelength band (for example, a wavelength band visible by those who are partially color-blind) in a visible region.

In a case where the optical device 30 has a wavelength selection function, the optical device 30 may include, for example, a wavelength selection filter that selectively transmits light in a predetermined wavelength band included in the light that has entered the optical device 30. Examples of the wavelength selection filter include a filter that attenuates ultraviolet light, a filter that attenuates infrared light, a filter that attenuates light in a predetermined wavelength band of visible light, or the like.

In a case where the optical device 30 has a wavelength distribution expansion function, the optical device 30 includes, for example, an optical component that makes it possible to expand a band of wavelength distribution included in the light that has entered the optical device 30 and distinguish a subtle color difference in the light that has entered the optical device 30.

[Effects]

In the following, description is given of the effects of the contact lens 2 of the present embodiment.

In the present embodiment, the functions applied to the glasses are provided in the contact lens 2. This makes it possible to respond to a violent motion or the like, while providing a predetermined action to the light entering the eyeball 100.

Furthermore, in the present embodiment, the optical device 30 that provides the action that is different from the action of the lens unit 10 to the light entering the eyeball 100 is mainly provided in a ring region 120B opposed to the outer edge of the pupil 120 that becomes large by expansion in a case where the lens unit 10 is placed on the eyeball 100. Accordingly, a user feels the effects of the optical device 30 only in a case where the pupil 120 becomes large in the dark environment. As a result, for example, it is possible to cause the user to feel, in the dark environment, an optical effect that is necessary and to prevent the user from feeling the optical effect that is rather not necessary in other environments (for example, the bright environment). Thus, in the present embodiment, it is possible to cause the user to feel, when necessary, the optical effect that is exerted in the glasses independent of the environment.

In addition, in the present embodiment, the optical device 30 provided in the lens unit 10 exhibits the function of, for example, the light volume amplification, the contrast emphasis, the wavelength conversion, the wavelength selection, or the expansion of the wavelength distribution. This makes it possible to cause the user to feel, when necessary (in the dark environment), the optical effect that is exerted in the glasses independent of the environment.

Moreover, in the present embodiment, the optical device 30 is provided within the lens unit 10. Accordingly, the presence of the optical device 30 makes it possible to prevent projections and depressions from being generated on the surface of the lens unit 10. Hence, it is possible to avoid worsening of the user's feeling of use of the contact lens 2 due to the presence of the optical device 30.

3. Third Embodiment

In the following, description is given of a contact lens 3 according to a third embodiment of the present disclosure. FIG. 9 illustrates an example of a condition in which the contact lens 3 is placed on the eyeball 100. The contact lens 3 includes the optical device 20 of the aforementioned embodiment and the optical device 30 of the aforementioned embodiment. In the present embodiment, the optical device 30 is provided on a circumferential rim of the optical device 20 and provides an action that is different from the action of the optical device 20. In the contact lens 3, for example, the optical device 20 is a device that performs light volume attenuation, and the optical device 30 is a device that performs light volume amplification. It is to be noted that, in the contact lens 3, for example, the optical device 20 may be a device that performs light volume attenuation and the optical device 30 may be a device that performs contrast emphasis. In addition, in the contact lens 3, for example, the optical device 20 may be a device that performs polarization separation, and the optical device 30 may be a device that performs light volume amplification. In addition, in the contact lens 3, for example, the optical device 20 may be a device that performs polarization separation, and the optical device 30 may be a device that performs contrast emphasis.

For example, this makes it possible to cause the user to feel, in the bright environment, the effects of the optical device 20 that are necessary in the bright environment and to prevent the user from feeling the effects of the optical device 20 that are rather not necessary in other environments (for example, the dark environment). Furthermore, for example, it is possible to cause the user to feel, in the dark environment, the effects of the optical device 30 that are necessary in the dark environment and to prevent the user from feeling the effects of the optical device 30 that are rather not necessary in other environments (for example, the bright environment). Thus, in the present embodiment, it is possible to cause the user to feel, when necessary, the optical effect that is exerted in the glasses independent of the environment.

In addition, a combination of the functions of the optical device 20 and the optical device 30 as described above makes it possible to achieve the contact lens 3 having multiple functions that are not achievable in the glasses.

4. Fourth Embodiment

In the following, description is given of a contact lens 4 according to a fourth embodiment of the present disclosure. FIG. 10 illustrates an example of a condition in which the contact lens 4 is placed on the eyeball 100.

The contact lens 4 includes the lens unit 10 to be placed on the eyeball 100 and an optical device 40 provided in the lens unit 10. The diameter of the lens unit 10 has a value larger than the diameter of the outer edge of the pupil 120. The lens unit 10 includes, for example, an optically transparent resin and has a role as a supporting base material that supports the optical device 40.

The optical device 40 is formed at, for example, at least the middle of the lens unit 10. The optical device 40 is mainly provided in a region opposed to the pupil 120, for example, in a case where the lens unit 10 is placed on the eyeball 100. That is, the optical device 40 is disposed at a position where the optical device 40 roughly covers the region opposed to the pupil 120 in any environment, for example. The optical device 40 is provided within the lens unit 10, for example. For example, the optical device 40 is circular-shaped as viewed from the front. It is to be noted that the optical device 40 may be in any shape other than a circular shape, and may be elliptically-shaped or polygonal-shaped, for example.

The optical device 40 is a device that provides an action that is different from an action of the lens unit 10 to the light entering the eyeball 100. The optical device 40 has a predetermined optical function with a small amount of visible light attenuation. The optical device 40 performs wavelength conversion, wavelength selection, or distribution of wavelength distribution, for example.

In a case where the optical device 40 has a wavelength conversion function, the optical device 40 includes, for example, a wavelength conversion film that converts ultraviolet rays included in light that has entered the optical device 40 to visible light (blue light, for example) or a wavelength conversion film that converts infrared rays included in the light that has entered the optical device 40 to visible light (red light, for example). In the case where the optical device 40 has the wavelength conversion function, the optical device 40 includes, for example, a wavelength conversion film that converts light included in the light that has entered the optical device 40 to a predetermined wavelength band (for example, a wavelength band visible by those who are partially color-blind) in a visible region.

In a case where the optical device 40 has a wavelength selection function, the optical device 40 may include, for example, a wavelength selection filter that selectively transmits light in a predetermined wavelength band included in the light that has entered the optical device 20. Examples of the wavelength selection filter include a filter that attenuates ultraviolet light, a filter that attenuates infrared light, or the like.

In a case where the optical device 40 has a wavelength distribution expansion function, the optical device 40 includes, for example, an optical component that makes it possible to expand a band of wavelength distribution included in the light that has entered the optical device 40 and distinguish a subtle color difference in the light that has entered the optical device 40.

[Effects]

In the following, description is given of the effects of the contact lens 4 of the present embodiment.

In the present embodiment, the functions applied to the glasses are provided in the contact lens 4. This makes it possible to respond to a violent motion or the like, while providing a predetermined action to the light entering the eyeball 100.

In addition, in the present embodiment, the optical device 20 provided in the lens unit 10 exhibits, for example, the predetermined optical function with a small amount of visible light attenuation, such as the wavelength conversion, the wavelength selection, or the expansion of the wavelength distribution. This makes it possible to provide the optical effects, which are beneficial to the user, without giving much influence on visibility.

5. Fifth Embodiment

In the following, description is given of a contact lens 5 according to a fifth embodiment of the present disclosure. FIG. 11 illustrates an example of a condition in which the contact lens 5 is placed on the eyeball 100.

The contact lens 5 includes the lens unit 10 to be placed on the eyeball 100, an optical device 50 provided in the lens unit 10, a sensor device 70 that senses a change in an external environment, and a control unit 60. The diameter of the lens unit 10 has a value larger than the diameter of the outer edge of the pupil 120. The lens unit 10 includes, for example, an optically transparent resin and has a role as a supporting base material that supports the optical device 50.

The control unit 60 controls a degree of an action (optical characteristics (viewing angle characteristics)) of the optical device 50 on the basis of a sensing signal outputted from the sensor device 70, for example. The sensor device 70 is, for example, a device that senses a position of the pupil 120 in the eyeball 100 or a device that senses blinks. In a case where the sensor device 70 is the device that senses the position of the pupil 120 in the eyeball 100, for example, the control unit 60 derives a direction or movement of a line of sight on the basis of the sensing signal (information regarding the position of the pupil 120 in the eyeball 100) inputted from the sensor device 70, and controls the optical characteristics (viewing angle characteristics) of the optical device 50 in accordance with the derived direction or the movement of the line of sight. In a case where the sensor device 70 is a device that senses blinks, for example, the control unit 60 derives the number or a frequency of blinks on the basis of the sensing signal (information regarding the blinks) inputted from the sensor device 70, and controls the optical characteristics (viewing angle characteristics) of the optical device 50 in accordance with the derived number or frequency of blinks.

The optical device 50 is formed at, for example, at least a middle of the lens unit 10. The optical device 50 is mainly provided in a region opposed to the pupil 120 in a case where the lens unit 10 is placed on the eyeball 100, for example. That is, the optical device 50 is disposed at a position where the optical device 50 roughly covers the region opposed to the pupil 120 in any environment, for example. The optical device 50 is provided within the lens unit 10, for example. For example, the optical device 50 is circular-shaped as viewed from the front. It is to be noted that the optical device 50 may be in any shape other than a circular shape, and may be elliptically-shaped or polygonal-shaped, for example.

The optical device 50 is a device that provides an action that is different from an action of the lens unit 10 to the light entering the eyeball 100. The optical device 50 exhibits, for example, the viewing angle characteristics that make an amount of blur in a peripheral portion of a visual field larger than the amount of blur in a central portion of the visual field by control of the control unit 60. FIG. 12 illustrates an example of a visual field of the user in a case where the contact lens 5 is placed on the eyeball 100. In FIG. 12, in a case where the user views the external environment through the optical device 50, a center of the visual field is a clear region 220 with relatively less blur, and a peripheral portion of the visual field is a blurred region 210 with relatively more blur. As illustrated in FIG. 13, for example, the optical device 50 functions as a device with the blur amount of 0% (with no blur) with respect to light entering from the front, and functions as a device with the blur amount gradually increasing in a case where a viewing angle exceeds a predetermined value.

An example of the optical device 40 that is able to provide the user with such a visual field is an optical device having characteristics in which aberration or haze varies depending on an entry angle of light. Such an optical device is an optical device having transmission characteristics dependent on the viewing angle, for example. The optical device having the transmission characteristics dependent on the viewing angle includes, for example, a liquid crystal layer having viewing angle characteristics, a device having entry angle characteristics with respect to transmission diffraction light (for example, a hologram device or a holographic PDLC (Polymer Dispersed Liquid Crystal: polymer dispersed liquid crystal)), or the like.

The optical device 50 may exhibit viewing angle characteristics that make an amount of blocked light in the peripheral portion of the visual field larger than the amount of blocked light in the central portion of the visual field by control of the control unit 60, for example. FIG. 14 illustrates an example of a visual field of the user in a case where the contact lens 5 is placed on the eyeball 100. In FIG. 14, in a case where the user views the external environment through the optical device 50, the center of the visual field is the clear region 220 with a relatively small amount of blocked light, and the peripheral portion of the visual field is the blurred region 210 with a relatively large amount of blocked light. As illustrated in FIG. 15, for example, the optical device 50 functions as a device with an amount of blocked light of 0% (with no blur) with respect to the light entering from the front, and functions as a device with the amount of blocked light gradually increasing in a case where the viewing angle exceeds a predetermined value.

[Effects]

In the following, description is given of the effects of the contact lens 5 of the present embodiment.

In the present embodiment, the contact lens 5 is provided with the optical device 50 having the viewing angle characteristics varying by control of the control unit 60. This makes it possible to respond to a violent motion or the like, while providing a predetermined action to the light entering the eyeball 100.

Furthermore, in the present embodiment, the lens unit 10 is provided with the optical device 50 that exhibits the viewing angle characteristics that makes the amount of blur in the peripheral portion of the visual field (blurred region 210) larger than the amount of blur in the central portion of the visual field (clear region 220). This makes it possible, for example, to prevent entry, to the user, of unnecessary information in the peripheral portion of the visual field and to cause the user to concentrate on necessary information in the central portion of the visual field.

In addition, in the present embodiment, the optical device 50 is provided within the lens unit 10. Accordingly, the presence of the optical device 50 makes it possible to prevent projections and depressions from being generated on the surface of the lens unit 10. Hence, it is possible to avoid worsening of the user's feeling of use of the contact lens 5 due to the presence of the optical device 50.

6. Sixth Embodiment

In the following, description is given of a contact lens 6 according to a sixth embodiment of the present disclosure. FIG. 16 illustrates an example of a condition in which the contact lens 6 is placed on the eyeball 100.

The contact lens 6 includes the lens unit 10 to be placed on the eyeball 100, and the sensor device 70 and an optical device 80 that are provided in the lens unit 10. The optical device 80 changes a degree of an action (optical characteristics) of itself (optical device 80) on the basis of a sensing signal outputted from the sensor device 70. The optical device 80 has a function common to, for example, the optical devices 20, 30, and 50 according to the aforementioned embodiments.

The optical device 80 is formed at, for example, at least a middle of the lens unit 10. The optical device 80 is mainly provided in a region opposed to the pupil 120 in a case where the lens unit 10 is placed on the eyeball 100, for example. That is, the optical device 80 is disposed at a position where the optical device 80 roughly covers the region opposed to the pupil 120 in any environment, for example. The optical device 80 is provided within the lens unit 10, for example. For example, the optical device 80 is circular-shaped as viewed from the front. It is to be noted that the optical device 80 may be in any shape other than a circular shape, and may be elliptically-shaped or polygonal-shaped, for example.

[Effects]

In the following, description is given of the effects of the contact lens 6 of the present embodiment.

In the present embodiment, the optical device 80 is provided in the contact lens 6. This makes it possible to respond to a violent motion or the like, while providing a predetermined action to the light entering the eyeball 100.

Furthermore, in the present embodiment, the lens unit 10 is provided with the optical device 80 that changes the degree of the action (optical characteristics) of the optical device 80 on the basis of the sensing signal outputted from the sensor device 70. This makes it possible to change the degree of the action (optical characteristics) of the optical device 80 in accordance with a change in the external environment, for example. As a result, it is possible to provide the user with a function in accordance with the change in the external environment.

7. Seventh Embodiment

In the following, description is given of a contact lens 7 according to a seventh embodiment of the present disclosure. FIG. 17 illustrates an example of a condition in which the contact lens 7 is placed on the eyeball 100.

The contact lens 7 includes the lens unit 10 to be placed on the eyeball 100, and the control unit 60 provided on the lens unit 10, a plurality of sensor devices 70, and an optical device 90 that are provided in the lens unit 10. The optical device 90 changes a degree of an action (optical characteristics) of the optical device 90 by control of the control unit 60. The optical device 90 has a function common to, for example, the optical devices 20, 30, and 50 according to the aforementioned embodiments.

The control unit 60 controls the degree of the action (optical characteristics) of the optical device 90 on the basis of a sensing signal outputted from each of the sensor devices 70, for example. Each of the sensor devices 70 is, for example, a device that senses sound pressure or an amount of heat. In a case where the sensor device 90 is a device that senses sound pressure, for example, the control unit 60 derives a direction in which the sound pressure is stronger, on the basis of the sensing signal inputted from each of the sensor devices 70, and controls the degree of the action (optical characteristics) of the optical device 90 in accordance with the derived direction. In a case where the sensor device 90 is a device that senses an amount of heat, for example, the control unit 60 derives a direction in which the amount of heat is larger on the basis of the sensing signal inputted from each of the sensor devices 7, and controls the degree of the action (optical characteristics) of the optical device 90 on the basis of the derived direction.

The optical device 90 is formed at, for example, at least a middle of the lens unit 10. The optical device 90 is mainly provided in a region opposed to the pupil 120, for example, in a case where the lens unit 10 is placed on the eyeball 100. That is, the optical device 90 is disposed at a position where the optical device 90 roughly covers the region opposed to the pupil 120 in any environment, for example. The optical device 90 is provided within the lens unit 10, for example. For example, the optical device 90 is circular-shaped as viewed from the front. It is to be noted that the optical device 90 may be in any shape other than a circular shape, and may be elliptically-shaped or polygonal-shaped, for example.

[Effects]

In the following, description is given of the effects of the contact lens 7 of the present embodiment.

In the present embodiment, the optical device 90 is provided in the contact lens 7. This makes it possible to respond to a violent motion or the like, while providing a predetermined action to the light entering the eyeball 100.

Furthermore, in the present embodiment, the lens unit 10 is provided with the optical device 90 that changes the degree of the action (optical characteristics) on the basis of the sensing signal outputted from each of the sensor devices 70. This makes it possible to change the degree of the action (optical characteristics) of the optical device 90 in accordance with a change in the external environment (change in the sound pressure or the amount of heat, for example). As a result, it is possible to inform the user of the change in the external environment (change in the sound pressure or the amount of heat, for example).

It is to be noted that the optical device 90 may be, for example, the optical device 20 according to the aforementioned embodiment or the optical device 30 according to the aforementioned embodiment. Even in such a case, it is also possible to inform the user of the change in the external environment (change in the sound pressure or the amount of heat, for example).

It is to be noted that, as illustrated in FIG. 18, for example, a light-emitting device 91 may be provided in place of the optical device 90. The light-emitting device 91 is provided in a region opposed to a circumferential rim of the iris 110, for example, in a case where the lens unit 10 is placed on the eyeball 100. The light-emitting device has a configuration in which a plurality of light-emitting units including, for example, a light-emitting diode, an organic electroluminescent device, or the like is annularly disposed. In this case, the control unit 60 controls light emission of the light-emitting device 91, for example, on the basis of a sensing signal inputted from each of the sensor devices 70. For example, the control unit 60 causes one or more predetermined light-emitting units of the plurality of light-emitting units in the light-emitting device 91 to emit light on the basis of the sensing signal outputted from each of the sensor devices 70. As illustrated in FIG. 18, for example, the control unit 60 causes a portion of the light-emitting device 91 to emit light 91A on the basis of the sensing signal outputted from each of the sensor devices 70. This makes it possible to inform the user of the change in the external environment (for example, the change in the sound pressure or the amount of heat) from a light-emitting position in the light-emitting device 91. In addition, in a case where the light-emitting device 91 is provided in the region opposed to the circumferential rim of the iris 110 in the case where the lens unit 10 is placed on the eyeball 100, it is possible to inform the user of the change in the external environment (for example, the change in the sound pressure or the amount of heat) without obstructing the visual field.

8. Modification Examples

In the following, description is given of the contact lenses 1 to 7 according to the aforementioned respective embodiments.

Modification Example A

In the aforementioned respective embodiments, as illustrated in FIG. 19, for example, the optical devices 20, 30, 40, 50, 80 or 90 may be disposed on a surface (concave-shaped surface 10B) on side in contact with the eyeball 100 of the lens unit 10 of the lens unit 10. In addition, in the aforementioned respective embodiments, as illustrated in FIG. 20, for example, the optical devices 20, 30, 40, 50, 80, or 90 may be disposed on a surface (convex-shaped surface 10A) on side not in contact with the eyeball 100 of the lens unit 10 of the lens unit 10. Even in a case where the optical device 20, 30, or 40 is disposed in such manners, it is possible to achieve various effects in the aforementioned respective embodiments may be achieved.

Modification Example B

In the aforementioned respective embodiments and the modification examples thereof, the contact lenses 1 to 7 may include the optical devices 20, 30, 40, 50, 80, and 90 each having a function for a left eye and a function for a right eye that are different from each other. For example, the optical devices 20, 30, 40, 50, 80, and 90 each having a relatively important function are provided in the contact lenses 1 to 7 used for a dominant eye of the user, and the optical devices 20, 30, 40, 50, 80, and 90 each having a supplemental function that is relatively less important are provided in the contact lenses 1 to 7 for an eye that is not the dominant eye.

It is to be noted that the effects described herein are merely illustrative. The effects of the present disclosure are not limited to the effects described herein. The present disclosure may have any effects other than the effects described herein.

Moreover, the present disclosure may have the following configurations, for example.

(1)

A contact lens including:

a lens unit to be placed on an eyeball; and a first optical device that is mainly provided in a circular region opposed to a pupil that becomes small by contraction in a case where the lens unit is placed on the eyeball, and provides an action that is different from an action of the lens unit to light entering the eyeball.

(2)

The contact lens according to (1), in which the first optical device performs polarization separation, light volume attenuation, wavelength conversion, wavelength selection, or expansion of wavelength distribution.

(3)

The contact lens according to (1) or (2), in which the first optical device changes a degree of the action in accordance with sound pressure or an amount of heat.

(4)

The contact lens according to any one of (1) to (3) further including:

a sensor device that senses a change in an external environment; and a control unit that controls the degree of the action of the first optical device on the basis of a sensing signal outputted from the sensor device.

(5)

The contact lens according to any one of (1) to (4), in which the first optical device is provided within the lens unit.

(6)

The contact lens according to any one of (1) to (5) further including:

a second optical device that is mainly provided in a ring region opposed to an outer edge of the pupil that becomes large by expansion in a case where the lens unit is placed on the eyeball, and provides an action that is different from the action of the lens unit to the light entering the eyeball.

(7)

A contact lens including:

a lens unit to be placed on an eyeball; and an optical device that is mainly provided in a ring region opposed to an outer edge of a pupil that becomes large by expansion in a case where the lens unit is placed on the eyeball, and provides an action that is different from an action of the lens unit to light entering the eyeball.

(8)

The contact lens according to (7), in which the optical device performs light volume amplification, contrast emphasis, wavelength conversion, wavelength selection, or expansion of wavelength distribution.

(9)

The contact lens according to (8), in which the optical device changes a degree of the action in accordance with sound pressure or an amount of heat.

(10)

The contact lens according to any one of (7) to (9) further including:

a sensor device that senses a change in an external environment; and a control unit that controls the degree of the action of the optical device on the basis of a sensing signal outputted from the sensor device.

(11)

The contact lens according to any one of (7) to (10), in which the optical device is provided within the lens unit.

(12)

A contact lens including:

a lens unit to be placed on an eyeball; and an optical device that is provided in the lens unit, and exhibits viewing angle characteristics that make an amount of blur in a peripheral portion of a visual field larger than an amount of blur in a central portion of the visual field.

(13)

The contact lens according to (12) further including:

a sensor device that senses a change in an external environment; and a control unit that controls a degree of the action of the optical device on the basis of a sensing signal outputted from the sensor device.

(14)

The contact lens according to (12) or (13), in which the optical device is provided within the lens unit.

(15)

A contact lens including:

a lens unit to be placed on an eyeball;

a sensor device that senses a change in an external environment; and an optical device that is provided in the lens unit, and changes a degree of an own action of the optical device on the basis of a sensing signal outputted from the sensor device.

(16)

A contact lens including:

a lens unit to be placed on an eyeball; and an optical device that is provided in the lens unit, and performs wavelength conversion, wavelength selection, or expansion of wavelength distribution on light entering the eyeball.

(17)

A contact lens including a lens unit to be placed on an eyeball;

a light-emitting device provided in the lens unit;

a sensor device that senses a change in an external environment; and a control unit that controls light emission of the light-emitting device on the basis of a sensing signal outputted from the sensor device.

(18)

The contact lens according to (17), in which the light-emitting device is provided in a region opposed to a circumferential rim of an iris in a case where the lens unit is placed on the eyeball.

This application claims the benefits of Japanese Priority Patent Application JP2017-199360 filed with the Japan Patent Office on Oct. 13, 2017, the entire contents of which are incorporated herein by reference.

It should be understood that those skilled in the art could conceive various modifications, combinations, sub-combinations, and alterations depending on design requirements and other factors, insofar as they are within the scope of the appended claims or the equivalents thereof.

The invention claimed is:

1. A contact lens, comprising:
a lens unit to be placed on an eyeball of a user;
a sensor device configured to:
sense a position of a pupil in the eyeball, and
output a first sensing signal based on the sensed position of the pupil in the eyeball;
a first optical device, wherein
the first optical device is in a circular region opposite to the pupil in a case where the lens unit is placed on the eyeball,
the first optical device is configured to:
provide a first action different from an action of the lens unit to light that enters the eyeball in a light incident direction,
change a degree of the first action based on an amount of heat, and
perform wavelength conversion of an invisible spectrum of the light that enters the eyeball to a visible spectrum of the light,
the circular region overlaps the pupil in the light incident direction in a state where the pupil is contracted, and
the first optical device is embedded within the lens unit such that the first optical device is spaced apart from the eyeball in the light incident direction;
a control unit configured to:
determine one of a direction or a movement of a line of sight of the user based on the first sensing signal outputted from the sensor device, and
control the degree of the first action of the first optical device based on the determined one of the direction or the movement of the line of sight; and
a second optical device in a ring region opposite to an outer edge of the pupil, wherein
the outer edge of the pupil becomes large by expansion in the case where the lens unit is placed on the eyeball,
the second optical device is configured to provide a second action different from the action of the lens unit to the light that enters the eyeball,
the second action includes one of attenuation of infrared light included in the light that enters the eyeball or expansion of a band of wavelength distribution included in the light that enters the eyeball, and
the second optical device is spaced apart from the first optical device.

2. The contact lens according to claim 1, wherein the sensor device is further configured to:
detect a change in an external environment, and
output a second sensing signal based on the detection of the change in the external environment, and
the control unit is further configured to control the degree of the first action of the first optical device based on the second sensing signal outputted from the sensor device.

3. The contact lens according to claim 1, wherein a function of the first optical device for a left eye is different from the function of the first optical device for a right eye.

4. A contact lens, comprising:
a lens unit to be placed on an eyeball of a user;
a sensor device configured to:
sense a position of a pupil in the eyeball, and
output a first sensing signal based on the sensed position of the pupil in the eyeball;
a first optical device in the lens unit, wherein
the first optical device is configured to:
perform wavelength conversion on light that enters the eyeball in a light incident direction, and
change a degree of the wavelength conversion based on an amount of heat, and
the first optical device is embedded within the lens unit such that the first optical device is spaced apart from the eyeball in the light incident direction;
a control unit configured to:
determine one of a direction or a movement of a line of sight of the user based on the first sensing signal outputted from the sensor device, and
control the degree of the wavelength conversion based on the determined one of the direction or the movement of the line of sight; and
a second optical device in a ring region opposite to an outer edge of the pupil, wherein
the outer edge of the pupil becomes large by expansion in a case where the lens unit is placed on the eyeball,
the second optical device is configured to provide an action different from an action of the lens unit to the light that enters the eyeball,
the action of the second optical device includes one of attenuation of infrared light included in the light that enters the eyeball or expansion of a band of wavelength distribution included in the light that enters the eyeball, and
the second optical device is spaced apart from the first optical device.

* * * * *